United States Patent [19]

Gamberg et al.

[11] 4,184,840
[45] Jan. 22, 1980

[54] ROTATABLE SUPPORTING STRUCTURE

[76] Inventors: Murray G. Gamberg; Aida Gamberg, both of 380 Taylors Mills Rd., Englishtown, N.J. 07726

[21] Appl. No.: 900,788

[22] Filed: Apr. 28, 1978

[51] Int. Cl.² .................................................. F27D 5/00
[52] U.S. Cl. .................................. 432/253; 432/258; 432/259; 269/54.5; 248/349; 264/57
[58] Field of Search .................... 432/253, 258, 259; 264/57, 58; 248/309 A, 349, 310, 346; 269/54.5, 71

[56] References Cited

U.S. PATENT DOCUMENTS

| 1,533,647 | 4/1925 | Hall | 274/1 E |
|---|---|---|---|
| 1,762,001 | 6/1930 | Turk | 432/259 |
| 2,751,951 | 6/1956 | Strathans | 269/54.5 |
| 3,004,745 | 10/1961 | Wilson | 248/349 |
| 3,486,629 | 12/1969 | Slaga | 248/349 |
| 3,948,594 | 4/1976 | Irwin, Jr. | 432/259 |
| 3,958,924 | 5/1976 | Egenolf et al. | 432/258 |
| 3,995,844 | 12/1976 | Hellman | 269/54.5 |
| 4,117,627 | 10/1978 | Slingerland, Jr. | 248/349 |

Primary Examiner—Henry C. Yuen
Attorney, Agent, or Firm—Howard N. Aronson

[57] ABSTRACT

A rotatable supporting structure adapted to withstand substantial intense heat and provide for the rotation of a workpiece without lateral displacement thereof during the heating of the workpiece within a furnace, including a base having a substantially planar upper surface, and a pin located on the upper surface of the base extending upwardly therefrom. The supporting structure also includes an upper member having an opening at substantially the center thereof, and of a diameter slightly larger than that of the cross sectional size of the pin. The upper member is provided with a plurality of holes or slots into which a plurality of supporting dowels may be disposed, in a variety of positions, thereby varying the space therebetween so as to support a workpiece without engaging the upper surface of the upper member and provide for the rotation thereof.

17 Claims, 9 Drawing Figures

U.S. Patent  Jan. 22, 1980  4,184,840
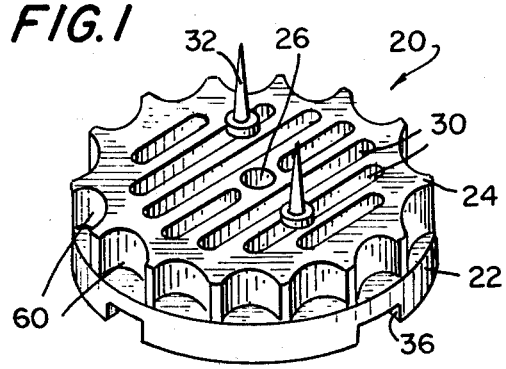
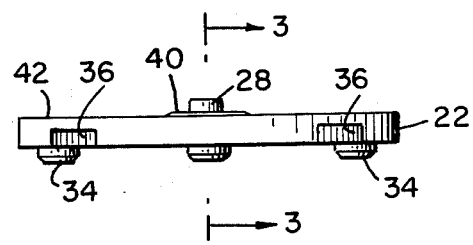
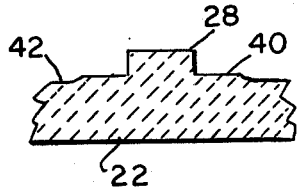
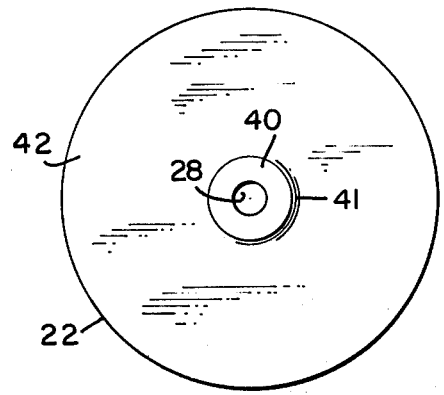
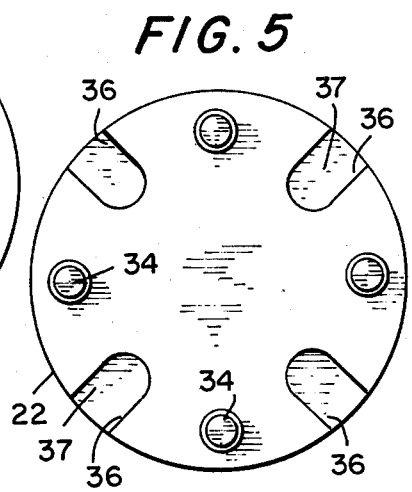
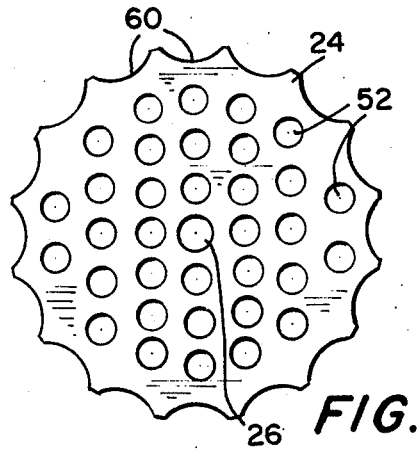
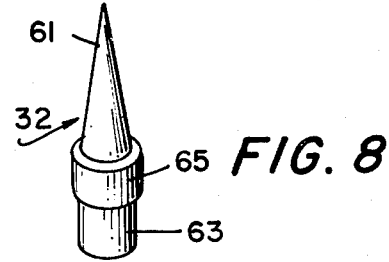
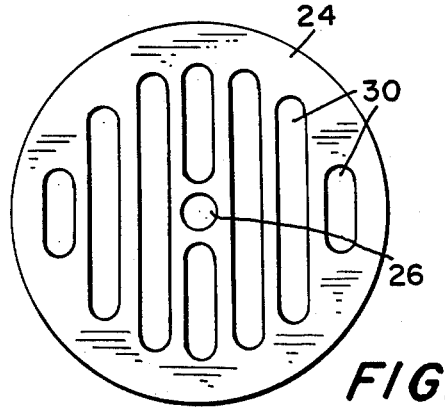
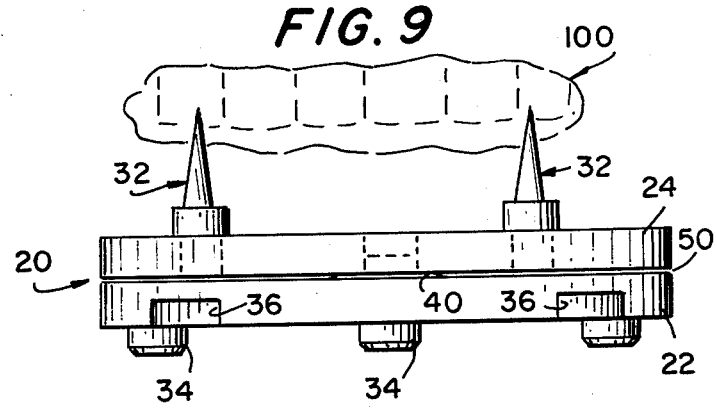

ROTATABLE SUPPORTING STRUCTURE

BACKGROUND OF THE INVENTION

1. Field of the Invention

The present invention relates to a rotatable supporting structure and more particularly to a ceramic supporting structure having portions adapted to engage dental bridgework made of porcelain which must be baked or fired during the production thereof. The supporting structure facilitates rotation of the workpiece without the necessity of removing or displacing it from its position within the furnace or oven utilized for curing the workpiece.

2. Description of the Prior Art

There are various types of supporting means which have been used in the past to support porcelain dental bridges or the like during the production thereof, while the porcelain is in its raw or pastelike state. The prior art support means are adpated with appendages which are adapted to engage the base metal supporting structure of the dental bridge and hold same keeping the porcelain in its paste form from engaging surfaces of the oven or the supporting means. Such prior art supporting structures are designed and adapted to hold the workpiece in one position only and it was necessary to move the entire supporting structure to move or rotate the workpiece in any manner. During the firing or curing of porcelain, in connection with the production of dental bridges, it is necessary to view or visually scrutinize the porcelain to determine the proper time for its removal from the oven or furnace.

It must be noted that during the heating of procelain in connection with the manufacture of bridgework, as each unit or workpiece is unique being made each individually, it is impossible to predetermine the exact amount of time which the procelain should be subjected to heat within a porcelain furnace or oven. The only way to accurately ascertain whether the proper amount of heat has been absorbed by the porcelain is by viewing the porcelain itself, which serves as a visual hardening indicator. When the porcelain is in its paste or soft state it is somewhat colorless, whereas as it absorbs heat it gains a whiteish tint. It is important during the curing of the porcelain that all portions thereof be heated to the proper degree during this initial curing, which is generally referred to in the art as the bisque bake. If parts of the porcelain have a modeled appearance it is an indication that it has not been cured to the proper degree. Generally, porcelain is applied to a base metal structure of the dental bridgework in varying depths, shapes and configurations. Therefore, portions of the procelain may be "cured" whereas other portions are not, a condition which must be avoided in order to produce a suitable product.

As is well known in the porcelain art, overbaking or curing subjects the porcelain to conditions which are undesirable structurally, and accordingly prompt removal of the porcelain at the point in time when all exposed surfaces visually indicate that the proper hardening has occurred, is required. In the past, as prior art supporting means held the bridgework in a stationary position, it was necessary to interrupt the curing or heating process by opening the furnace door, and completely removing the supporting structure with the workpiece disposed thereon, to the oven door or other open surface. To accomplish such a removal, suitable prongs or tweezers are required to hold the supporting means or move it into various positions so that one could look at all sides or 360° of the workpiece. The removal of the workpiece from the oven, in order to properly view all angles of the bridgework, presented severe disadvantages as the heat loss associated with removing the workpiece from the oven is generally in the area of 400°–600° F. Such a severe reduction in temperature causes the porcelain to acquire glass build-up due to the silicon present in most porcelain materials. In the past, heating and reheating was required in order to allow for the inspection of the workpiece, and normally it was necessary to reheat two or three times in order to find the correct amount of curing. Accordingly, cracking of the porcelain, due to glass build-up was common which necessitated the discarding of the workpiece. As is appreciated in the art, glass build-up due to reheating greatly increases the likelihood of a defective finished product and greatly increases the cost of production.

It is, of course, possible to merely open the door of the heating oven or furnace in order to view the workpiece without moving it, which results in a heat loss of only 50°–70° F., but it is then impossible to view all sides of the porcelain. If the workpiece is removed too early, it is then necessary to re-introduce the workpiece as described above, which shocks the porcelain introducing glass build-up, which severely weakens the structure as well as causing surface deformities and large structural cracks. If the workpiece is left to remain in the oven too long, glass build-up is also promoted.

Also required for the preparation of porcelain bridgework is a glaze bake coating which is applied to the porcelain or a subsequent glaze bake. After the second coating or glaze bake the workpiece must then be fired at a temperature most often times higher than that at which it was cured and again, the glaze bake must be visually viewed in order to determine the proper point at which to remove the workpiece. Generally, during the two firing procedures discussed, it is common to remove the workpiece from ten or fifteen times in order to determine the proper time at which the various curing or firing steps have been completed.

During the bisque bake as well as the glaze bake it should be noted that a temperature drop in the area of 50°–70° F., which occurs when the oven door is opened only, does not affect the porcelain or the glaze coating and accordingly the oven door may be opened an unlimited number of times without causing any damage to the workpiece. However, heat loss in the area of 400°–600° F. which occurs when the workpiece is moved out of the oven for inspection does cause severe problems and structural and physical damage to the workpiece, and in some instances damage beyond the point where the product can be used.

SUMMARY OF THE INVENTION

The present invention overcomes the disadvantages of the prior art supporting means by providing a rotatable supporting means which may be easily rotated within conventional porcelain ovens or furnaces, which furnaces due to the high temperature and intense heat required normally are three inches wide, five inches high, and approximately five inches deep. Accordingly, being able to rotate the workpiece without removing it from the oven completely eliminates heat losses in excess of 50°–70° F., and allows for proper direct viewing of the visual indications of the porcelain during all curing and firing steps required in making porcelain dental bridgework.

The structure of the present invention features a base having substantially planar upper surface, and having a pin located on the upper surface extending upwardly therefrom. There is provided an upper member having an opening at the center thereof which opening is of a diameter slightly larger than that of the pin. There are movable supporting means located on the upper surface of the upper member which are adapted to hold porcelain workpieces away from the supporting structure and the surfaces of the oven so that the wet or pastelike porcelain can be subjected to heat as evenly as possible. The upper member may be rotatably disposed on the base which remains stationary throughout the entire firing operation whereby the upper member may be readily, easily and smoothly rotated so that all sides of the workpiece may be viewed without having to remove same from the oven.

It is an object of the present invention to provide a supporting structure which can be readily rotated within conventional porcelain furnaces and ovens and which can withstand the intense heat and repeated heatings.

Furthermore, it is an object of the present invention to provide a supporting means which will enable the workpiece to be rotated within conventional ovens for viewing. Furthermore, as at the rear of conventional ovens the heat is the greatest, rotating the workpiece allows for even heating of all surfaces without having to laterally displace the supporting means.

Another object of the present invention is to provide a supporting structure made of a ceramic material that facilities its easy removal from the oven due to its configuration and which may be smoothly and readily rotated without the supporting structure tending to displace.

It is a further object of the present invention to provide a movable supporting means on the upper portion of the upper member so that a large variety of differently shaped workpieces may be readily accommodated. The supporting means are preferably movable such that the distance between supporting structures is readily changeable.

Still further objects and features of the present supporting means reside in the provision of a two piece rotatable structure whereby the base frictionally engages the base of the ceramic furnace to resist being displaced, whereas the upper member disposed thereon is readily rotatable.

These, together with the various ancillary objects and features of the invention which will become apparent as the following description proceeds, are attained by this rotatable supporting structure, preferred embodiments of which are shown in the accompanying drawing, by way of example only, wherein:

BRIEF DESCRIPTION OF THE DRAWINGS

FIG. 1 is a perspective view of a preferred embodiment of a rotatable supporting structure made in accordance with the present invention including several dowels disposed thereon to facilitate the supporting of a workpiece;

FIG. 2 is a side elevational view of the base thereof;

FIG. 3 is a partial vertical cross-sectional view taken along the plane 3—3 in FIG. 2;

FIG. 4 is a top plan view of the base;

FIG. 5 is a bottom plan view of the base;

FIG. 6 is a top plan view of the upper member;

FIG. 7 is a top plan view of an alternate embodiment of the upper member;

FIG. 8 is a perspective view of a preferred embodiment of a supporting dowel, and FIG. 9 is a side elevational view of the supporting structure shown with a workpiece disposed thereon.

DETAILED DESCRIPTION OF THE INVENTION

With continuing reference to the accompanying drawing wherein like reference numerals designate similar parts throughout the various views, reference 20 is used to generally designate a rotatable supporting structure constructed in accordance with the concepts of the present invention. The supporting structure 20 includes a base 22 and an upper member 24 which has an opening 26 therein, which upper member is disposed upon the base whereby it is rotatably supported thereon. The base 22 includes a pin 28 which is at least partially disposed within the opening 26 when the upper member 24 is mounted on said base 22.

The upper member 24 includes, in the preferred embodiment, a plurality of elongated slots 30, into which a plurality of supporting dowels 32 may be disposed and displaced laterally with respect to one another such that the spacing between dowels 32 may be readily and easily changed. It is noted that either one or more dowels 32 may be utilized as required to accommodate and support various workpieces of various shapes.

All components of the rotatable supporting structure may be manufactured of a suitable ceramic material such that it will withstand temperatures in the area of 2500° F. and above. Generally, any ceramic material which can be cast, machined, or pressed into the desired structural shape as set forth herein, and which can withstand temperatures in the area of 2500° F. are suitable in connection with the present invention, materials such as Cordierite, Dichorite, or Iolite ($4(Mg.Fe)0.4Al_2O_3 10SiO_2H_2O$). A ceramic material such as Cordierite manufactured by Corning Glass Company has been found to provide a suitable material with which to construct the base, upper member and dowels of the present invention.

By way of explanation, it should be understood that the present invention may be utilized for supporting workpieces of a variety of types and kinds which are to be subjected to intense heating, such as dental bridgework comprised of porcelain applied to a supporting base metal. However, the present invention is useful and intended for use in connection with a wide variety of products which require heating during the production thereof. It is in connection with the baking or firing of the porcelain with which the rotatable supporting structure provides distinct advantages over prior art methods and apparatus of supporting procelain or other structures during heating, by enabling one to rotate the workpiece without having to laterally displace same or remove it from the heating furnace.

As discussed previously herein, providing a means for rotating a porcelain workpiece during the various heating or baking steps thereof while it is retained in the oven provides distinct advantages and eliminates severe disadvantages present in prior art methods and apparatus used in connection with porcelain products. The present invention is particularly suited for manufacturing dental products comprised at least partially of porcelain as it is desirable to view all surfaces of the irregular and unique hand-made items prior to removing same from the furance.

As noted above, most conventional ceramic materials are suitable for manufacturing the components of this rotatable supporting means, if said ceramics can withstand temperatures up to 2500° F. However, it is preferable that the ceramic contain as little air as possible as prolonged and frequent heating and cooling may cause the ceramic to crack or undergo catastrophic failure after many reheatings.

In the manufacture of porcelain products the present invention has been found particularly useful in connection with most conventional heating furnaces such as known in the industry as a Ney-Barkmeyer furnace manufactured by J.M. Ney Company or ceramic furnaces as manufactured by New York Dental Manufacturing Company. Most conventional furnaces for use in the preparation of dental bridges maintain a sub-atmospheric pressure during heating temperatures from room temperature to 1700° F. Thereafter, atmospheric pressure is maintained and it is possible to open the doors of the furnace during the heating, and it is during the heating process over and above 1700° F. that it is normally necessary to visually view the workpiece being produced.

As may be easily seen in FIG. 2, the base 22 of the supporting means includes a plurality of legs 34, (and as shown in FIG. 5 which is a bottom plan view of the base) the legs 34 are somewhat evenly spaced across the bottom surface of member 22. As the base 22 is intended to remain stationary while the upper member 24 rotates thereon the legs 34 facilitate supporting the base on the bottom of the furance floor, or the like, and further serve to grip or form a frictional engagement with the surface of the heating furnace whereby manual rotation of the upper surface will not cause movement or rotation of the base 22.

There is also provided at the lower surface of the base at the outer edges thereof a plurality of depressions 36 which extend from the outer periphery of the base inwardly therefrom. The depressions 36 serve to reduce the thickness of the base at its outer edge such that conventional gripping means, such as tongs or tweezers can easily engage and grip the base. It must be appreciated that when the upper member is disposed on the base, in order to easily pick up or displace the supporting means after it has been exposed to intense heat for some period of time, that tweezers or tongs or the like are required and that as the base 22 and member 24 are movable with respect to one another, it is desirable to grip the base only during handling with tweezers, or the like. The depressions 36 reduce the thickness or the distance between the upper surface of the upper member 24 and the general lower surface of the base such that at the perimeter of the supporting means, at the location of the depressions 36, the distance between the upper surface 42 and the lower surface of the base 37 at the location of the depressions is reduced to readily receive the prongs of a tweezer.

A pin 28 is located at substantially the geographic center of the base 22 and surrounding the pin is a raised portion or bearing surface 40 which serves to facilitate rotation of the upper member without movement of the base. As may be readily seen in FIG. 4, in the preferred embodiment, the bearing surface 40 completely surrounds the pin 28 and extends radially outwardly therefrom.

The raised portion, traveling away from the pin 28 towards the edge of the base, tapers off gradually into the substantially planar upper surface of the base. The bearing surface 40 is raised only a slight distance above the level of the generally planar upper surface 42 of the base, but it is intended to engage the lower surface of the upper member which surrounds the opening 26 therein such that the upper member is substantially solely supported thereby. Generally, the raised portion extends from the pin to a point where it engages the planar upper surface of base 22 a distance approximately one tenth of the radius of the base 22. However, the raised portion 40 may be of any desired shape and configuration deemed desirable in connection with the complementary surface of the upper member which it engages (surrounding opening 26). The bearing surface 40 need only raise the substantially planar lower surface of the upper member 24 a small distance above surface 42 such that there is not coextensive engagement between the lower surface of the upper member 24 and the upper surface 42 of the base during rotation. It must be understood that the upper member 24 will rotatably or movably engage the stationary pin during use about the exterior side surface of pin 28 at raised portion 40 and, possibly at the upper surface 42 of base 22 at the outer edge of the upper member at only a smally portion thereof if there is sufficient weight on the upper surface to cause the upper surface to tilt and bear on surface 42 during rotation. However, a large area of coextensive engagement is eliminated between member 22 and 24 during use.

As may be seen in FIG. 9, the workpiece 100 may be supported by the rotatable supporting means 20 via the supporting dowels 32 which engage any suitable portion or area of the workpiece 100 such that the porcelain surfaces thereof will not engage the base or the walls of the firing furnace. With the upper member 24 engaging the bearing surface 40 there is created a slight space 50 between the facing surface of the base and the upper member. The limited area of engagement between the two members (at surface 40) of the supporting means reduces the frictional engagement therebetween and facilitates rotation of the upper member while the lower member remains stationary. Even if the weight of the workpiece 100 should be off-center and cause the center of gravity of its weight to be located on a portion which is not over the bearing surface 40, the base 22 and the upper member 24 will only be tilted or displaced a very slight distance whereby members 22 and 24 would engage at only one point at the perimeter thereof and not create a large additional area of mutual engagement which would defeat ready rotation of the upper member.

The upper member 24, as may be readily seen in FIG. 6, preferably has a scalloped or irregular outer shape which facilitates engaging the upper member with a tweezer, or the like, to effect rotation as well as providing areas of reduces radial size 60 which, when placed directly above a depression 36 will allow one to engage the base 22 with a tweezer without having to grip the upper member. It must be understood that the upper member 24 may have any desirable shape such as conventional geometric shapes (triangular, square or rectangular or the like) as well as being circular and of a diameter equal to, greater than or less than the diameter of the base 22. Preferably, the upper member 24 includes at least one portion of reduced radial size 60 whose radius is less than that of the base above the depression 36 so that a portion of the base is easily accessible to tweezers.

To facilitate supporting the workpiece the upper member 24 has a plurality of holes therein 52 which there may be placed the supporting dowels 32. As seen in FIG. 6, there is provided a plurality of holes 52 such that it is possible to create various spacings between the supporting dowels 32 when there are two or more of such dowels utilized, so that it is possible to engage all types and shapes of workpieces. However, it must be understood that various arrangements of holes 52, and various other types of supporting means may be utilized in connection with the rotatable supporting structure. As seen in FIG. 7, there may be provided a plurality of slots 54 such that the supporting dowels or the like may be disposed therein and readily moved laterally along the slots that the spacing between dowels 32 may be easily changed, and provides for a wide range of spacings to be created between the dowels 32.

As may be seen in FIG. 8, the supporting dowel 32 may include a conical upper portion 61 and a lower cylindrical rod portion 63. The dowel also may include an outwardly extending lip 65 of a diameter greater than the diameter of holes 52 or greater than the transverse size of the slots 54. The lip 65 may be of any desired shape such as square, rectangular or the like, but the disc-like or circular configuration is preferred. As may be readily understood, one or more dowels 32 may be disposed in one or more slots 54, or disposed in several holes 52 in the upper member 24.

A latitude of modification, substitution and change is intended in the foregoing disclosure, and in some instances, some features of the present invention may be employed without a corresponding use of other features.

We claim:

1. A ceramic rotatable supporting structure for use with intense heat comprising a ceramic base having a substantially planar upper surface, a ceramic pin located on the upper surface of said base extending upwardly therefrom and stationary with respect thereto, a slightly raised bearing surface completely surrounding said pin, a ceramic upper member having an opening at substantially the geographic center thereof, said opening being of a diameter slightly larger than the cross-sectional size of said pin, ceramic means for supporting a workpiece located on the upper surface of said upper member whereby the upper member may be totatably disposed on said base with said pin extending into said opening such that said upper member rotates about said pin.

2. A ceramic rotatable supporting structure as in claim 1, wherein said pin and said upper member are intergal.

3. A ceramic rotatable supporting structure as in claim 1, wherein all components of said supporting structure are of a ceramic material which will withstand temperatures in excess of 2500 degrees F.

4. A structure as in claim 1, wherein said slightly raised bearing surface is intergal with said base.

5. A structure as in claim 3, wherein said bearing surface at its periphery tapers gradually downwardly into the upper surface of said base.

6. A structure as in claim 1, wherein said pin is circular in cross-section.

7. A structure as in claim 1, wherein said opening is circular.

8. A structure as in claim 1, wherein there are at least three ceramic legs located on said base and depending therefrom.

9. A structure as in claim 1, wherein said base has a plurality of indented portions in the lower surface thereof commencing at the outer edge of said base and extending towards the center of said base whereby the thickness of the edge of the base at said indentations is reduced.

10. A structure as in claim 1, wherein said base is substantially circular.

11. A structure as in claim 1, wherein the upper member has a substantially planar lower surface.

12. A structure as in claim 1, wherein the upper member is substantially circular.

13. A structure as in claim 1, wherein the upper member is of a diameter less than that of the diameter of said base.

14. A structure as in claim 1, wherein the edge of said upper member is scalloped so as to vary the radial size of said member at various locations along the edge of said upper member.

15. A structure as in claim 1, wherein the upper member has a plurality of holes therethrough to receive said supporting means therein.

16. A structure as in claim 1, wherein the upper member has a plurality of elongated slots to receive said supporting means therein.

17. A structure as in claim 1, wherein the supporting means includes a plurality of elongated ceramic dowels each having a supporting lip to engage the upper surface of said upper member.

* * * * *

UNITED STATES PATENT OFFICE
CERTIFICATE OF CORRECTION

PATENT NO. : 4,184,840
DATED : January 22, 1980
INVENTOR(S) : Murray G. Gamberg; Aida Gamberg It is certified that error appears in the above-identified patent and that said Letters Patent are hereby corrected as shown below:

IN THE CLAIMS:

Claim 1, line 12, Delete "totatably" and insert

--rotatably--.

Signed and Sealed this

Twenty-seventh Day of May 1980

[SEAL]

Attest:

SIDNEY A. DIAMOND

Attesting Officer

Commissioner of Patents and Trademarks